(12) United States Patent
Rusin et al.

(10) Patent No.: US 10,720,233 B2
(45) Date of Patent: Jul. 21, 2020

(54) WEB-ENABLED DISEASE-SPECIFIC MONITORING

(71) Applicant: Medical Informatics Corp., Houston, TX (US)

(72) Inventors: Craig Rusin, Houston, TX (US); Emma Fauss, Houston, TX (US)

(73) Assignee: Medical Informatics Corp., Houston, TX (US)

( * ) Notice: Subject to any disclaimer, the term of this patent is extended or adjusted under 35 U.S.C. 154(b) by 402 days.

(21) Appl. No.: 14/548,405

(22) Filed: Nov. 20, 2014

(65) Prior Publication Data

US 2015/0142464 A1    May 21, 2015

Related U.S. Application Data

(60) Provisional application No. 61/906,716, filed on Nov. 20, 2013.

(51) Int. Cl.
*G16H 15/00* (2018.01)
*G16H 10/60* (2018.01)

(52) U.S. Cl.
CPC ............. *G16H 15/00* (2018.01); *G16H 10/60* (2018.01)

(58) Field of Classification Search
CPC ...... G06Q 50/22; G06Q 50/24; G06F 19/322; G06F 19/3487; G06F 17/248; G06F 17/211; G16H 10/60; G16H 15/00
USPC .................................................... 705/2, 3, 4
See application file for complete search history.

(56) References Cited

U.S. PATENT DOCUMENTS

| | | | |
|---|---|---|---|
| 2005/0020886 A1* | 1/2005 | Hutchinson | A61B 5/00 600/300 |
| 2005/0055243 A1* | 3/2005 | Arndt | G06F 19/3418 705/2 |
| 2006/0015261 A1* | 1/2006 | Mann | G01N 33/4905 702/19 |
| 2010/0131293 A1* | 5/2010 | Linthicum | G06Q 50/24 705/3 |
| 2010/0281107 A1 | 11/2010 | Fallows et al. | |
| 2012/0278099 A1* | 11/2012 | Kelly | G16H 10/60 705/3 |

FOREIGN PATENT DOCUMENTS

WO    WO-2010089307 A1 *  8/2010    ............ A61M 5/142

OTHER PUBLICATIONS

Van Ham, Frank, "Perceptual Organization in User-Generated Graph Layouts," IEEE Transactions on Visualization and Computer Graphics, vol. 14, No. 6, Nov./Dec. 2008 (Year: 2008).*

* cited by examiner

*Primary Examiner* — John P Go
(74) *Attorney, Agent, or Firm* — Schafer IP Law

(57) ABSTRACT

A set of applications can access a specific patient's real-time or historical physiological data from a clinical care unit and calculate new disease specific physiological indicators or be a virtual physiological monitor for that patient. The applications are run on a remote server and push the resulting data to an endpoint device.

23 Claims, 6 Drawing Sheets

WEB-ENABLED DISEASE-SPECIFIC MONITORING

TECHNICAL FIELD

The present invention for Web-Enabled Disease-Specific Monitoring (DSM) relates to the field of medical care, and in particular to a technique for accessing a patient's real-time physiological data and calculating a disease-specific physiological index or a virtual physiological monitor for that patient.

BACKGROUND ART

Current patient monitoring has not changed significantly over the last 30 years. While sensor technology has improved and expanded, the monitoring technology itself has gone through the evolution from paper line tracings to CRT to LCD displays. But the way the data has been displayed has not significantly changed over that time (i.e. the line on the paper is the same line that is displayed on the LCD screen). Doctors face a fundamental challenge that the information they need to answer very specific clinical questions is not presented to them in an intuitive way.

There are physiological measurements that directly measure the body using sensors that record measurements like heart rate, respiration rate, blood pressure, etc. There are also physiological measurements or indexes that are calculated by combining direct measurements; examples include the pressure reactivity index (PRx) and the starling curve (the ability of the heart to change its force of contraction and therefore stroke volume in response to changes in venous return). Medical Researchers often discover new physiological relationships which they render as an index or scale.

However, when one wants to present a new physiological index or present the calculated data in a novel way (a novel Virtual Monitor (VM)), the only way at present is to build a new instrument, take the instrument through the Food and Drug Administration (FDA) certification process and clinical trials, and attempt to sell it on the open market. Current solutions are based on a one algorithm-one device model, which is physically unscalable beyond more than a few algorithms with their associated sensory devices.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
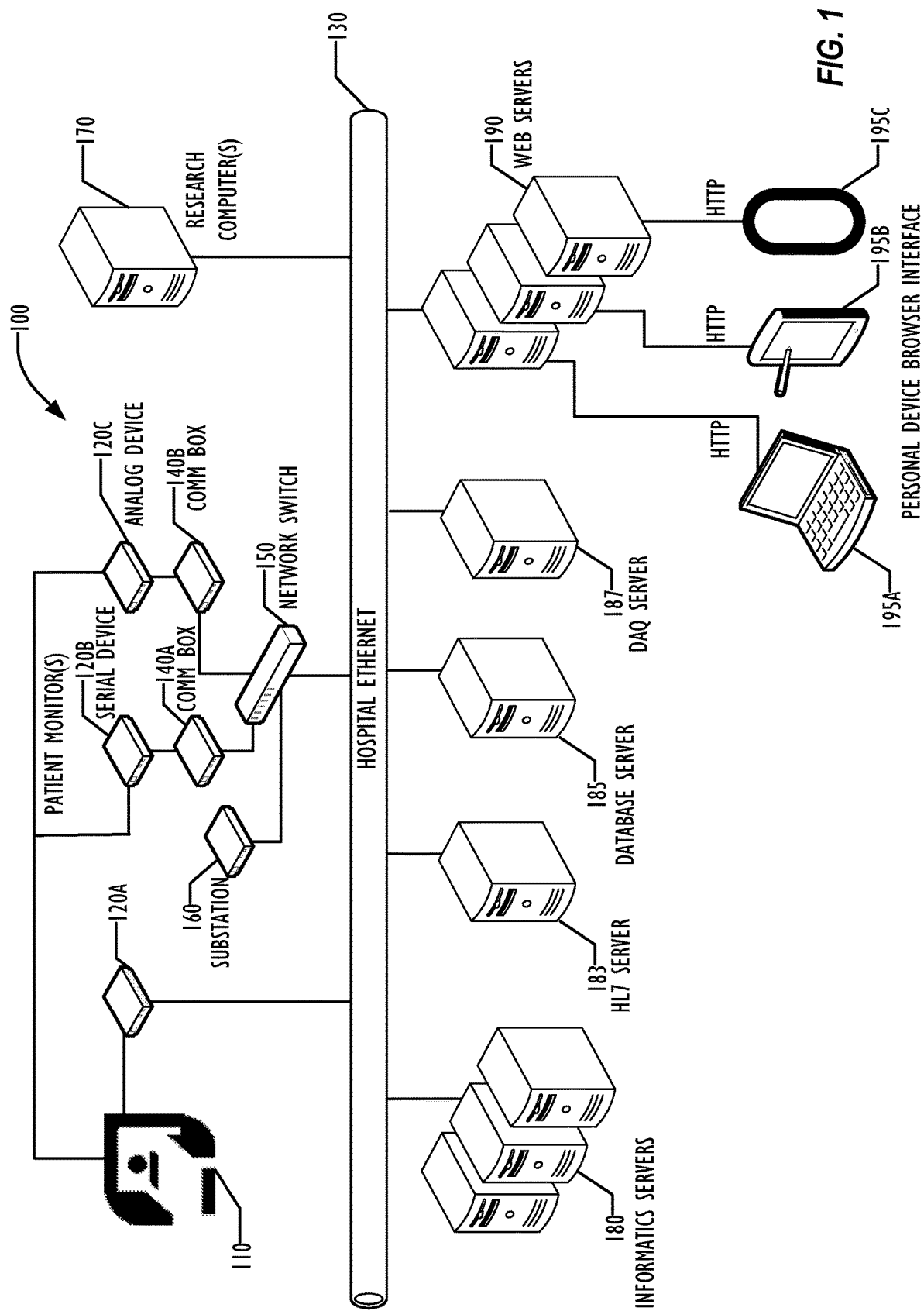
FIG. 1 is a block diagram illustrating a network of devices employed by a hospital system according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes and may not have been selected to delineate or circumscribe the inventive subject matter; resort to the claims is therefore necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Some current middleware vendors have limited access to device data and often downsample the data to such an extent that it makes meaningful analytics impossible. An example of the data they help capture is patient vital signs (e.g. heart rate, respiratory rate) taken every minute and then pushed to the hospital's electronic medical records (EMR) for storage. EMR storage of patient-specific historical data is very limited in terms of the data that is collected (low resolution, downsampled data from only supported networked devices) as well as its inability to conduct data analysis either retrospectively or in teal-time.

When one product captures and stores patient bedside monitoring data, its data format is proprietary and closed. It provides a single tool which converts the data files into enormous XML files, which the end-user must parse to retrieve specific information. This task is unmanageable for research. Additionally other products may export to Health Level 7 (HL7), a text based format which is equally unsuitable for research. (HL7 refers to a set of international standards for transferring clinical and administrative data between hospital information systems, and are produced by Health Level Seven International, Inc.) There are limitations of such systems: such systems do not have a reliable timestamp and provide data through a spreadsheet with a limited viewing tool rather than through an analysis-friendly tool. Additionally, such systems do not have the ability to capture data from ancillary, non-networked patient monitoring devices.

Another product redisplays bedside monitor data in real-time for clinical use but does not archive the data for research or make it available for analysis. It also does not have the ability to capture data from ancillary, non-networked devices. It also does not have the ability to export this data for subsequent analysis.

The system described herein can capture all the physiological data on the network and on any monitor device with a serial or analog port. The majority of physiological monitoring devices have a serial or analog port. For purposes of this discussion, a serial device is one that provides a serial, non-networked output and an analog device is a non-networked device that provides an analog output signal. Embodiments of the system timestamp the data in its archive to within a predetermined level of accuracy, allowing synchronization of data and analysis of data across the various input sources. The system can perform calculations on the data in real-time.

Embodiments of the system can provide the data to a external numerical computing environment available to researchers for analysis, in addition to providing its own data analysis tools. One such external environment is the MATLAB® environment. (MATLAB is a registered trademark of The Mathworks, Inc.)

The system comprises five types of servers, in addition to various data acquisition devices: data acquisition servers, database servers, informatics servers, and visualization servers. Embodiments may employ one or more of each type of server. In addition, external computers, may connect to the system for research analysis of the collected data.

A structured query language (SQL) database is used to hold the index for data storage location in the file system, rather than the actual data files. A unique technique assures both networked and non-networked devices provide timestamps for data that are accurate and synchronized to within 40 milliseconds, allowing correlating collected data.

In one embodiment, a clinical research format (CRF) data format allows recording of an arbitrary number of signals with an arbitrary frame-rate with an arbitrary sampling rate, where
1) The number of signals can vary per frame;
2) The number of samples can vary per signal per frame;
3) Each signal has a unique identifier; and
4) Users can create their own set of unique identifiers;

Different frames can have different data types, for example picture, numeric array, eXtended Markup Language (XML), Java Script Object Notation (JSON), text, binary, etc. The data format allows for inclusion of calibration constants.

Embodiments of the system can use distributed processing for real-time physiological data processing, where real-time distributed processing means physiological and associated patient data can be distributed among an arbitrary number of machines for parallel processing and continuous transformation with low latency. For example, a program may be created to process real-time data, which may be designated to run on one of a plurality of informatics servers. The system then executes the program on the designated informatics server. For purposes of this discussion, "real time" is used to mean that "without perceivable delay."

The system can push physiological data to web browsers in real time through a websocket protocol that facilitates real-time 2-way interaction between an informatics server and a web browser. The system converts incoming physiological data streams from various data sources at bedside monitors to the CRF data format. Then the CRF data can be converted to JSON and pushed to a websocket server, which then can use a publish/subscribe model to publish the data to all client browsers in real time. The distribution is push-based, instead of pull-based, allowing distribution to multiple web browsers simultaneously.

The system allows for distributed collection of data from non-networked (serial and analog) devices with buffering. A distributed system allows converting native device data into the CRF format, which is then pushed to a central server for collection and routing. All data collection is synchronized and time stamped. In some embodiments, a medical device sends data to a computer, which sends data to a switch, which sends data to sub-station computer which sends data to data collection server. The substation is used to identify what devices are associated with a particular bed. This bed association allows integrating non-networked data signals with other networked data signals.

The system allows for alarm routing. Alarms are captured by the system, typically as HL7 streams.

Arbitrary calculations may be applied to data streams in the CRF format, transforming the data streams for recognizing false positives and false negatives, as well as for displaying data and new derived metrics. This allows rapid creation of new monitors and monitoring modalities for different users or different diseases. In addition, data fusion of physiological data, labs and medications allows the system to present new alarms and new monitors that may be patient or disease specific, using different pieces of patient data to create new alarms and new monitors. Various embodiments provide the capability of easily combining an arbitrary number of data signals and transforming them into useful information for the user, providing new monitoring modalities.

Data is obtained from various sources, converted to CRF format, and collected in real-time and stored on data servers, allowing data transformation to occur in real-time or on historical data sets.

Various embodiments allow creation of modular monitoring or virtual monitoring, which can be one or more of disease- and patient-specific monitoring, based on the condition of the patient, as defined or decided by a care provider. A doctor can prescribe a type of monitoring on a patient-by-patient basis. Monitor data can be accessed remotely through a website interface.

Data transformations are done on the server; display transformations may be done by a website interface. Multiple transformations can be computed in parallel for a particular patient. Raw data is transcoded into CRF format, routed or distributed to informatics servers, where it can be transformed data using arbitrary transformation. The transformed data can itself be recursively re-routed or distributed, transcoded again, and turned into visualized data.

Distributed clock synchronization is a feature that allows correlating data from a hierarchical network of devices, each with a clock with a certain, possibly different, precision. Because the clocks may drift over time the system uses the Network Time Protocol (NTP) to synchronize data acquisition servers. In one embodiment, the data acquisition servers contacts every substation in every patient room every minute.

In one embodiment, the Data Acquisition (DAQ) server opens a connection to a substation, typically an Internet protocol suite connection, such as a Transmission Control Protocol (TCP) connection. The DAQ server acquires its current time stamp and transfers it to the substation. The substation records its timestamp when the transmission is completed and sends the DAQ server the substation timestamp and the timestamp received from the DAQ server. The DAQ server then calculates the time differential. This procedure is repeated multiple times, and the lowest time differential is sent back to the substation from the DAQ server. The substation uses that differential to reset its internal clock. When the substation received a new time offset, it executes the same procedure to synchronize all of the connected serial or analog devices.

This technique is performed repeatedly. In one embodiment, the technique is replicated every minute, on every substation. The frequency of time synchronization depends on the precision of the internal clocks of the devices in the system, including the substations.

Real-time physiological data can be pushed to any number of clients. A client can subscribe to a data channel as one or both of a data sink and a data source. An arbitrary number of clients can subscribe to a single channel and a single client can subscribe to an arbitrary number of channels. In one embodiment, this is implemented in the informatics server, which provides a multi-threaded distributed system, providing for failover detection and recovery for real-time processing. The informatics system monitors every instantiated process on the informatics server(s) and recognizes when the process abnormally terminates and automatically restarts it.

In one embodiment, the DAQ server polls each archive (informatics) server and requests the amount of free space on each server. Then the DAQ server transfers the file to the informatics server with the most available space. All data acquired for a bed is transferred together to prevent data fragmentation. This helps evenly distribute the data among the existing archive servers.

Websocket server(s) provide a native interface. Data is transcoded from CRF to JSON which is transmitted to the websocket server(s).

Real-time calculations (e.g., new metrics of health) executed on the system can be pushed to HL7 data streams in compliance with international health care informatics standards. Arbitrary calculations may be computed on the informatics servers, the result of which can generate and emit an HL7 message.

The combination of servers allows for modular construction of monitoring from widgets that allow arbitrary display and graphing of data from arbitrary data streams. Modular construction of monitors is provided by using layouts and modular, re-useable widgets for physiological data and other metrics of health, which may or may not be calculated from other physiological data. The professional user, such as a physician, can define their own customized monitor using the modular construction of monitoring. This can be applied on a patient-by-patient basis. Embodiments provide for real-time transcoding of CRF data format to formats such as JSON, HTML, XML, TXT, and HL7 as well as other data formats as desired, and provide the ability to decode and encode the CRF format into various other formats. This allows HL7 integration into an internal data stream. HL7 messages can be decoded into the CRF format and be processed like every other data frame in the system.

Embodiments allow visualization of transformed physiological and patient related data, including both calculated data and measured data. New types of data visualization (e.g., non-standard monitor views) can be generated. The system also provides support for novel metrics of health, such as goal-directed therapies and predictive analytics.

FIG. 1 is a block diagram illustrating a system 100 for collecting, archiving, and processing arbitrary data in a healthcare environment according to one embodiment.

As illustrated, there are five types of servers: the DAQ server 187, the informatics server(s) 180, the database server 185, the HL7 server 183, and the web server(s) 190. Any number of any of the types of servers may be deployed as desired. All of the servers 180-190 connect to each other and the bedside monitors via one or more hospital networks 130. Although illustrated as a single hospital Ethernet network 130, any number of interconnected networks may be used, using any desired networking protocols and techniques.

Also connected to the hospital network 130 are a number of bedside monitors for monitoring physiological data for a patient in bed 110. These bedside monitors may include network connected monitors 120A, which can deliver digital physiological data to the hospital network 130, serial devices 120B, which produce digital data but are not directly connected to a network, and analog devices 120C, which produce analog data and are not directly connected to a network. Communication boxes 140A and 140B allow connecting the serial devices 120B and analog devices 120C, respectively, to the hospital network 130, typically through a network switch 150. In addition, a substation 160 may be also connected to the network 130 via the network switch 150 for performing data manipulation and time synchronization as described below. Any number of bedside monitor devices 120 may be used as determined advisable by physicians and other clinical staff for the patient in bed 110.

Although as illustrated in FIG. 1 the bedside monitors and associated communication devices are connected directly or indirectly to the hospital network 130, remote bedside monitoring devices may be used as part of the system 100, such as home monitoring devices, connected to the hospital network 130 indirectly through the Internet or through other communication techniques.

Additionally, one or more research computers 170 may be connected, directly or indirectly, to the hospital network 130, allowing researchers to access aggregated data collected from bedside monitors 120 for performing analytics and development.

The web servers 190 are configured for communicating with personal devices such as laptop 195A, tablet 195B, or smart phone 195C via a web browser interface using HyperText Transport Protocol (HTTP).

Figure 2:
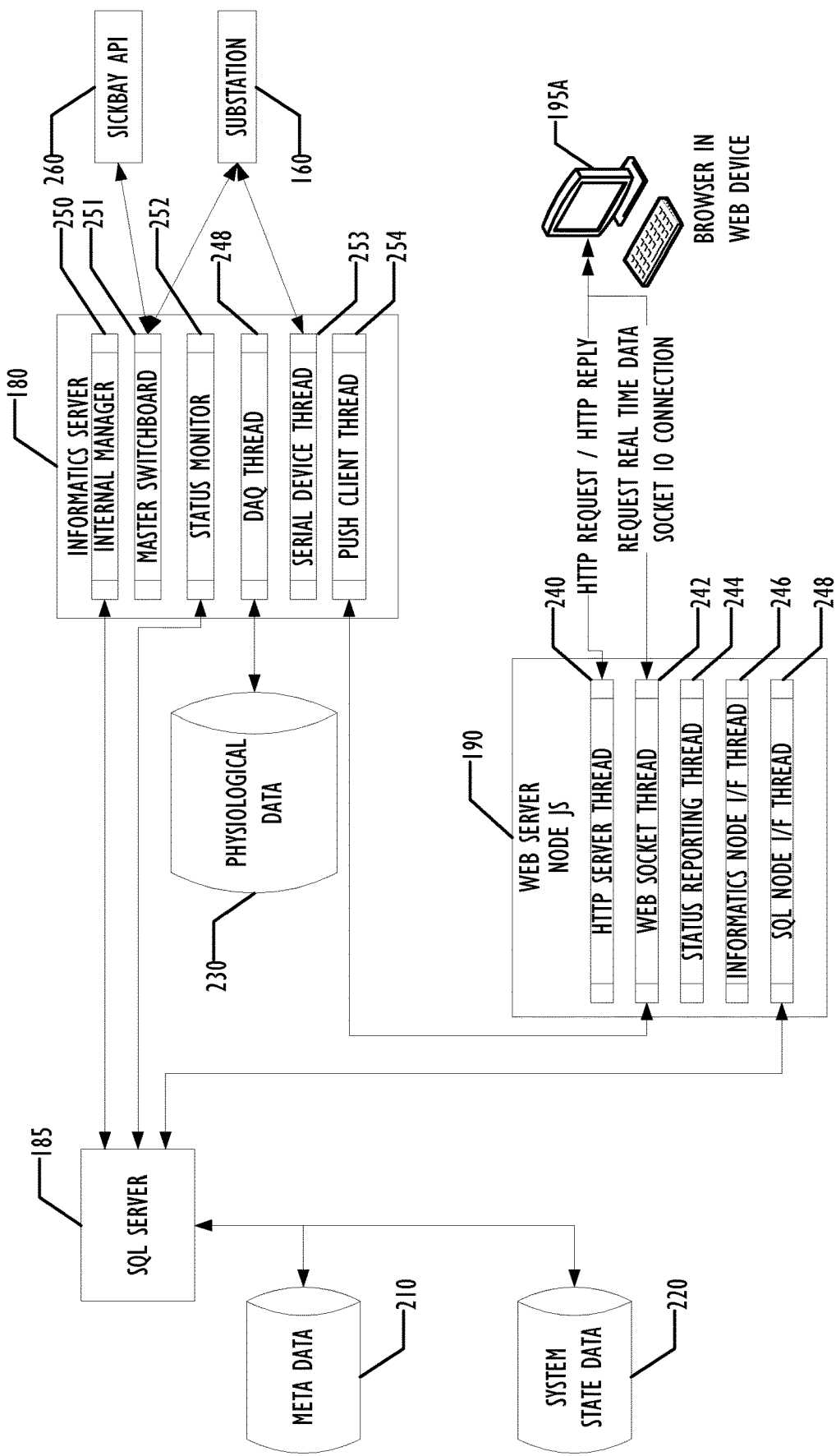
FIG. 2 is a block diagram illustrating communication flows in a hospital system according to one embodiment.

Further details are illustrated in FIG. 2, which is a block diagram illustrating communication flows in the system 100 according to one embodiment. The database server 185 in one embodiment is a Structured Query Language (SQL) server, managing two data collections: metadata 210 and system state data 220. As explained above, rather than keeping the actual patient data in the server 185, the server 185 stores index information pointing to the actual physiological data stored by the informatics server(s) 180. As illustrated in FIG. 2, a storage device is used by the SQL server 185 for storing metadata 210 and a different storage device used for storing system state data 220; however, any number of storage devices may be used, and metadata 210 and system state data 220 may be stored on shared devices as desired and configured for performance purposes. Although illustrated as an SQL server, the database server 185 may use other database technology for storing the metadata 210 and system state data 220 as desired. If an SQL server is used, any type of SQL database system may be used, including PostgreSQL.

Similarly, FIG. 2 illustrates a single storage device 230 for physiological data as binary data, wave forms, etc.; however, any number of storage devices may be used as desired. As described above, multiple informatics servers and multiple storage devices may be used, distributing the data across multiple servers and storage devices as desired for performance reasons.

In one embodiment, the web server 190 may use multiple threads for performing its task of providing an interface to the monitored data. An HTTP server thread 240 may handle HTTP requests and replies for communicating with browsers in user devices 195, such as the laptop 195A illustrated in FIG. 2. Similarly, a websocket thread 242 may be employed for real time data socket I/O connections. Additionally, status reporting thread 244, informatics server node interface thread 246, and database node interface thread 248 may be employed in the web server 190. Similarly, the informatics server 180 may be multi-threaded, with an internal manager thread 250 for communicating with the SQL server 185, a master switchboard thread 251 for communicating with an Application Programming Interface (API) 260 and substations 160, a status monitor thread 252 for monitoring the status of the SQL server 185, a serial device thread 253 for communicating with the substation 160, and a push client thread 254 for communicating with the web socket thread of the web server 190.

Figure 3:
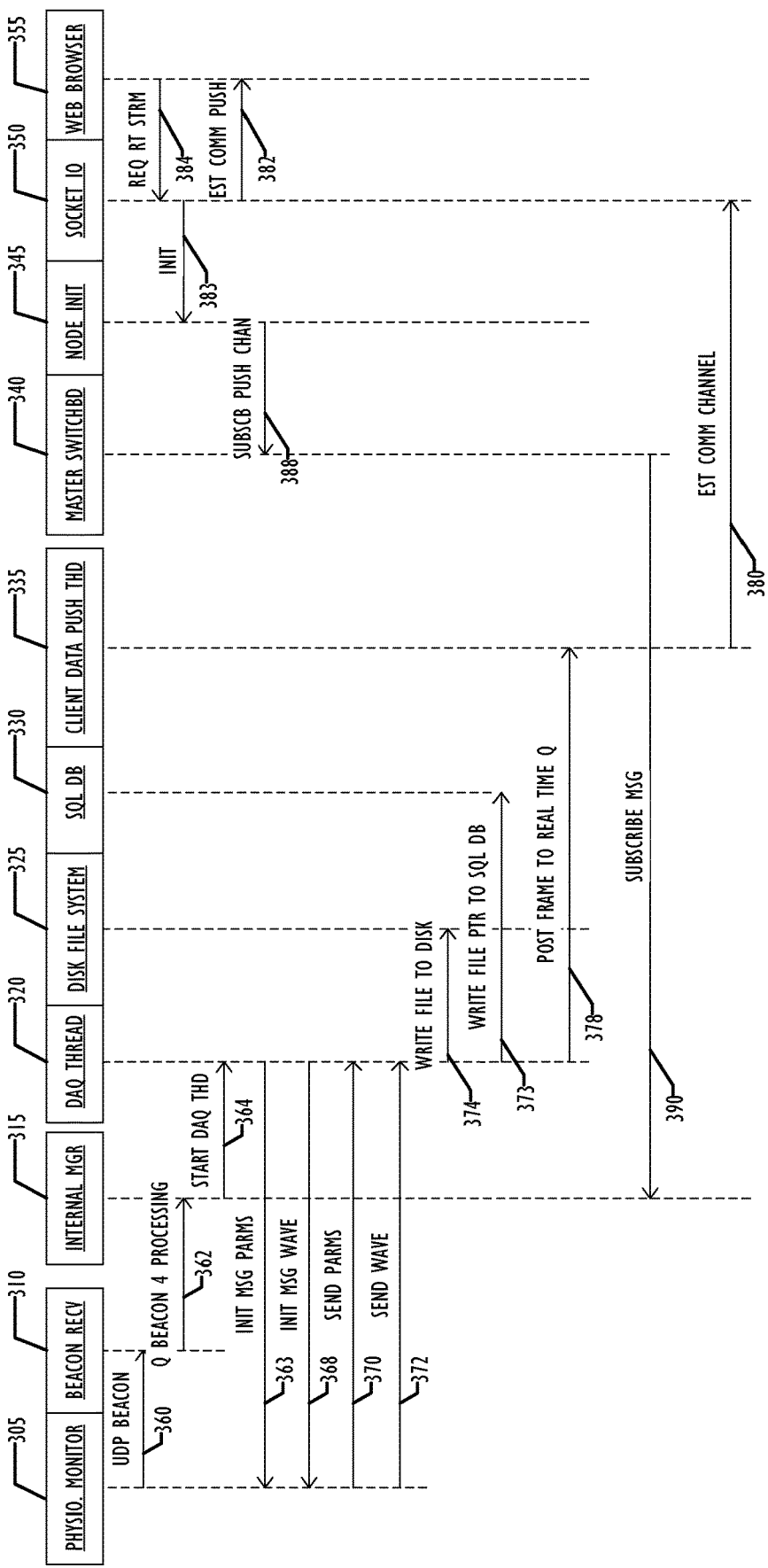
FIG. 3 is a sequence diagram illustrating patient monitor to web browser communication according to one embodiment.

FIG. 3 is a Unified Modeling Language (UML) sequence diagram illustrating bedside monitor to web browser communications in the system 100 according to one embodiment. Physiological monitor 305, which corresponds to one of the bedside monitors 120 of FIG. 1 sends a beacon message 360 to a beacon receiver object 310 in DAQ server 187, which in turn sends a queue beacon for processing message 362 to an internal manager thread 315 of an informatics server 180. The internal manager thread 315 sends a message to a data acquisition thread 320 of the data acquisition server 187 to start acquiring data. The data acquisition thread 320 sends messages 366-372 to the physiological monitor 305, telling the monitor 305 to initialize parameters and waveforms (366, 368), then the monitor 305 sends parameters and waveforms (370, 372) to the data acquisition thread 320. Upon receiving physiological data, the data acquisition thread 320 writes (374) a data file to a disk file system 325 of the informatics server 180 and writes (376) a file pointer to the data file to the SQL database 330 of the database server 185. The data acquisition thread also posts a CRF frame to a real time queue (378) of a client data push thread 335. That thread sends a message (380) to a socket I/O thread 350 of the web server 190 to establish a communication channel. The socket I/O thread 350 sends a establish communications push thread 382 to the web browser 355 of one of the user devices 195, causing it to send a request for a real-time stream (384) back to the socket I/O thread 350.

The socket I/O thread 350 sends an initialization messages 386 to a node initialization object 345, causing it to send a subscribe to push channel messages 388 to master switchboard thread 340. The master switchboard thread 340 then sends a subscribe message 390 to the internal manager thread 315 of the informatics server 180.

Figure 4:
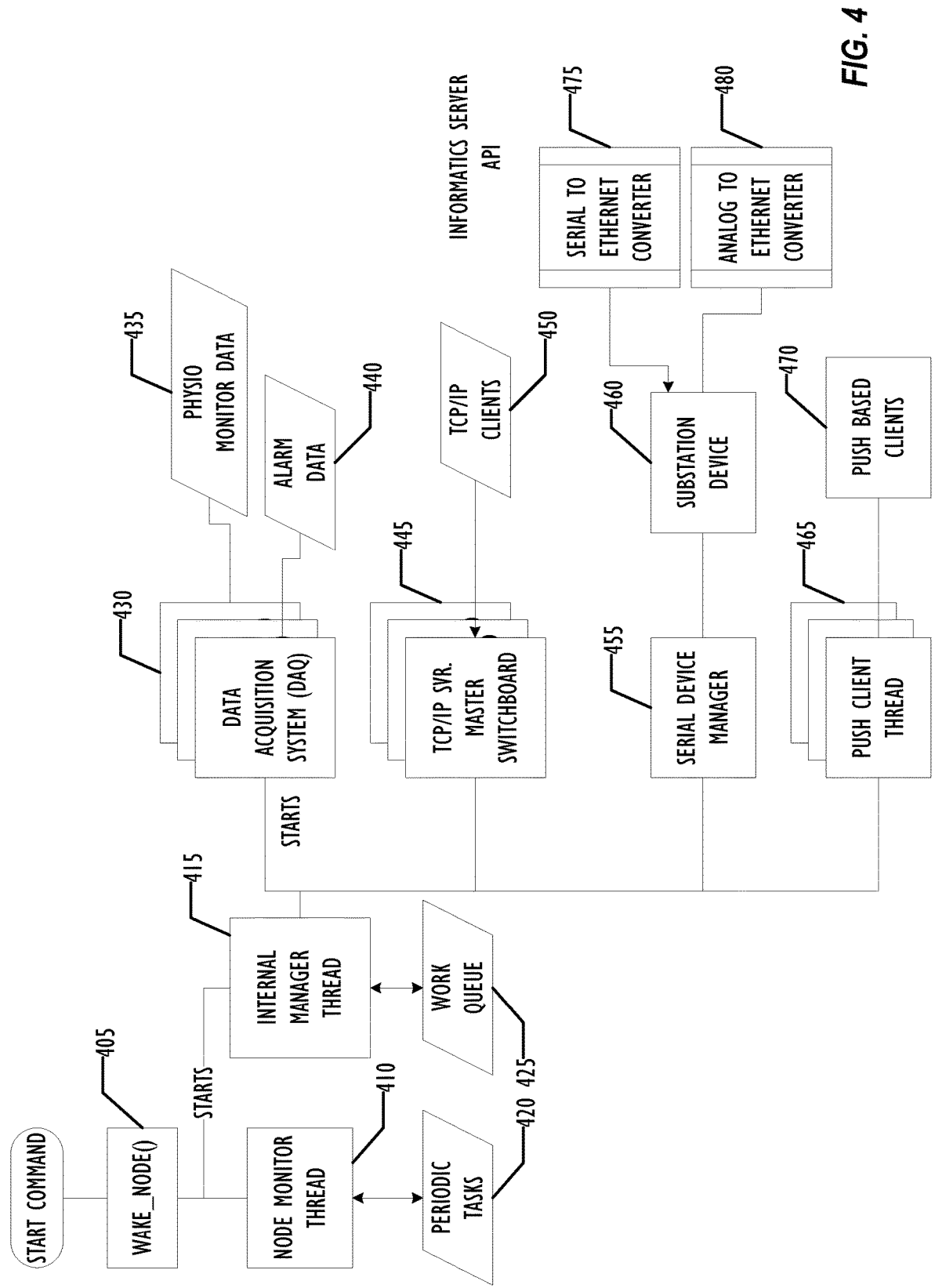
FIG. 4 is a flowchart illustrating a sequence of events occurring during startup of a hospital system according to one embodiment.

FIG. 4 is a flowchart illustrating initialization of the system 100 according to one embodiment. Starting on the informatics server 180, the primary thread of the system 100 is the wake-node thread 405, which is started by a start command. The wake-node thread 405 starts two other threads: the node monitor 410 and the internal manager 415.

The node monitor thread 410 has a list of periodic tasks that the system 100 needs to do, and the node monitor thread 410 places these tasks as commands in an internal manager thread work queue 420. The internal manager thread 415 has a work queue 425 that contains a ranked list of tasks or commands which the internal manager 415 executes by starting new threads.

The internal manager thread 415 starts the following threads:

1) Data Acquisition (DAQ) Subsystem 430, which acquires physiological monitor data 435 and alarm data 440. In one embodiment, the DAQ thread 430 executes on the data acquisition server 187.

2) TCP/IP Server (or Master Switchboard) 445. This thread starts TCP/IP clients 450.

3) Serial Device Manager thread 455. This thread interacts with the substations 460 (corresponding to substations 160 of FIG. 1), which in turn interact with serial to Ethernet converters 475 and analog to Ethernet converters 480, corresponding to the communications boxes 140A, 140B of FIG. 1.

4) Push Client thread 465. This thread interacts with push-based clients 470.

Each of these threads can in parallel read and write to the file system of the informatics server(s) 180 and can in parallel read and write to the SQL database maintained by the database server 185.

The DAQ thread 430 listens on the network for network packets from physiological monitors on the hospital network. Each time a packet is received, its contents are examined to extract the bed identifier, the location on the network, as well as services the device supports. The bed identifier within the packet is compared to the bed filter list maintained by the server informatics server 180. The bed filter list is the list of all bed identifiers for which the server 180 is responsible for recording data. The bed filter list is periodically synchronized with the database table DAQ bed filter. All network packets with bed identifiers which are not on this list will be ignored.

All network packets with bed identifiers within the filter list will be enabled for recording. In one embodiment, when the main data acquisition thread 430 encounters a packet which identifies an active bed which matches the filter criteria and is not currently being recorded, a new DAQ thread 430 is created. In such an embodiment, therefore, the system 100 starts one data collection thread 430 for each bed 110 to be recorded. This new thread 430 will record all of the data being generated from the bed 110.

Network sockets are established for each device for data communication. Multiple vital sign signals can be found in a single packet. Typically multiple signals can be found in each waveform packet. In one embodiment, each signal can be sampled at rates ranging from less than 0.2 Hz to greater than 1 KHz.

The data acquisition system (430) can process packets slightly out of order and overlook lost packets. Each packet has a sequence number associated with it. Additionally, the time between data packets is not necessarily constant. As a result, the data collection system 430 needs to have a way to correct for packet jitter. Since each packet contains data which is evenly sampled, the number of samples can be used as a clock to ensure that the data timestamp is accurate. Drift is expected since the clock on the bedside device 120 is not exactly the same as the server 187's internal clock. Each minute, the offset between the two clocks can be estimated and the clocks re-synced thereby eliminating DAQ clock drift. In addition, where bedside devices, such as serial devices 120B or analog devices 120C do not have clocks, the substation 160 may be used to inject clock data into the packets. Clock drift is similarly handled for packets processed by the substation 160 by synchronizing the clocks periodically.

Time synchronization is done using a distributed hierarchical time synchronization technique. Data acquisition substation devices 160 each have their own master clock and those clocks are synched to a time synchronization server using NTP on a per room basis. Where sensors 120 produce serial or analog data without timestamp data, a converter box (such as communication box 140A/B) is used to add a timestamp. In some embodiments, each hospital room has a data acquisition substation 160 that communicates with the other devices in the room using the network switch 150. The substation's clock may also be synchronized with the data acquisition server 187's clock to avoid time drift, as discussed above.

The DAQ threads 430 also listen for alarms 440 posted on the network and manages the bed list listening for bed assignments and changes in bed assignment.

The Master Switchboard thread 445 uses a high performance architecture for providing asynchronous communication with clients. Clients can include, but are not limited to a MATLAB interface for communicating with the research server 170, and the system web servers 190, and a C Application Programming Interface (API) library which can be integrated into third party programs such as the LABVIEW® software (LABVIEW is a registered trademark of National Instruments Company).

The Serial Device Manager thread 455 manages data from all the serial and analog non-networked devices 120B and 120C that communicate via substations 460. Periodically, this thread will check the status of all of the serial and analog data collection devices on the network. In one embodiment, HTTP retrieval is performed for records as well as websockets (signals, labs, meds) using a representational state transfer (REST) interface.

The serial device manager thread 455 also can perform remote firmware upgrades when necessary, and synchronize the clock on the non-networked devices with the local master clock on the server 187, and push out additional configuration settings if necessary.

The Push Client Manager thread 465 manages all of the outgoing push-based data streaming clients. When a new push-based client (e.g., a websocket client) is registered, thread 465 creates an outgoing connection to the specified IP address, using the specified protocol. All data from the specified channel is then automatically pushed to this outgoing client connection whenever new data is available. Data is also automatically transcoded into the desired format. In one embodiment, for websocket-based clients, all data is transcoded into JSON format.

In one embodiment, the system 100 uses an SQL database to hold all of the state full information regarding all system operations. The other servers poll the database for changes in its state.

The system webserver(s) 190 enable standard web browsers to access all the functionality of the system 100. The system webserver 190 in one embodiment is built on top of the Node.JS® platform (NODE.JS is a registered trademark of Joyent, Inc.) and is composed of two components, an HTTP server which serves the web pages associated with the system 100, and the WebSocket server which provides the mechanism for real-time data streaming from the informatics server to the client's browser 195. The real-time data streaming uses a publish-subscribe architecture for disseminating real-time physiological data to web clients.

Figure 5:
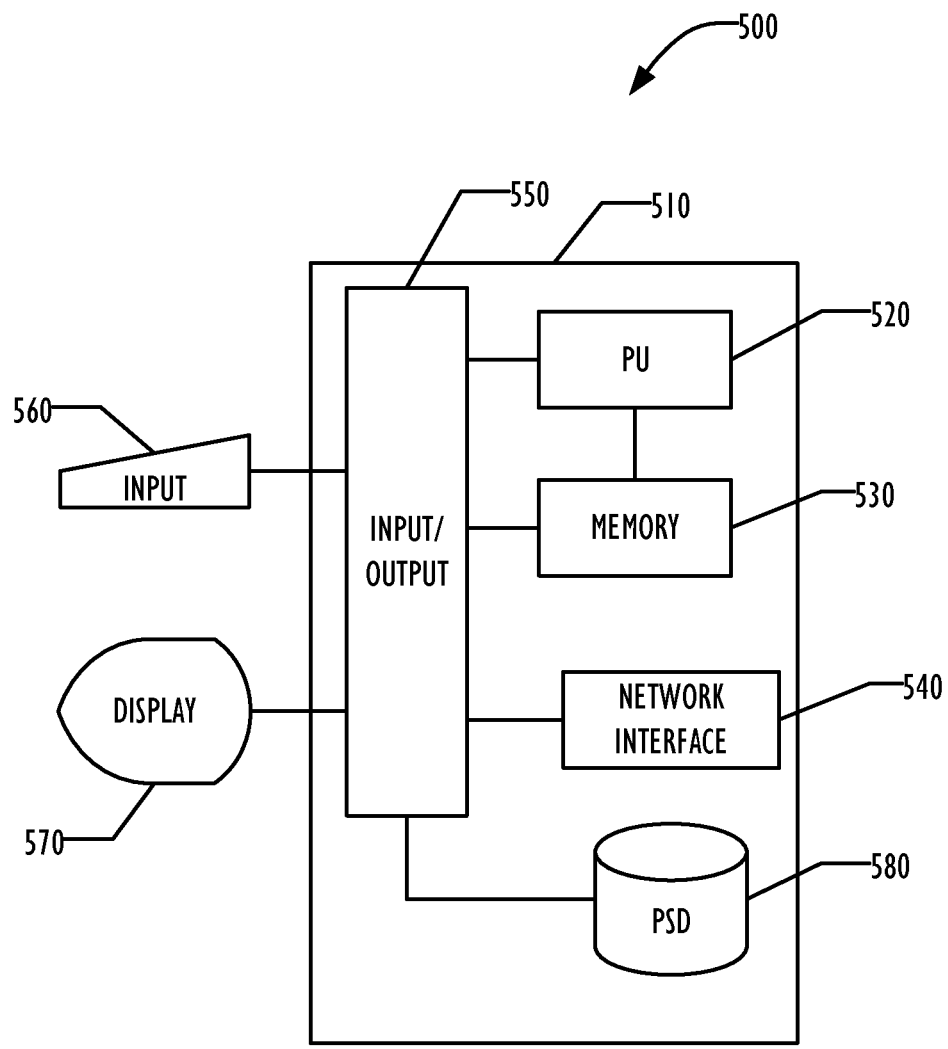
FIG. 5 is a block diagram illustrating a computer system for use in implementing one or more embodiments.

Referring now to FIG. 5, an example computer 500 for use as one of the servers 180-190 is illustrated in block diagram form. Example computer 500 comprises a system unit 510 which may be optionally connected to an input device or system 560 (e.g., keyboard, mouse, touch screen, etc.) and display 570. A program storage device (PSD) 580 (sometimes referred to as a hard disc) is included with the system unit 510. Also included with system unit 510 is a network interface 540 for communication via a network with other computing and corporate infrastructure devices (not shown). Network interface 540 may be included within system unit 510 or be external to system unit 510. In either case, system unit 510 will be communicatively coupled to network interface 540. Program storage device 580 represents any form of non-volatile storage including, but not limited to, all forms of optical and magnetic, including solid-state, storage elements, including removable media, and may be included within system unit 510 or be external to system unit 510. Program storage device 580 may be used for storage of software to control system unit 510, data for use by the computer 500, or both.

System unit 510 may be programmed to perform methods in accordance with this disclosure (an example of which is in FIG. 4). System unit 510 comprises a processor unit (PU) 520, input-output (I/O) interface 550 and memory 530. Processing unit 520 may include any programmable controller device, such as microprocessors available from Intel Corp. and other manufacturers. Memory 530 may include one or more memory modules and comprise random access memory (RAM), read only memory (ROM), programmable read only memory (PROM), programmable read-write memory, and solid-state memory. One of ordinary skill in the art will also recognize that PU 520 may also include some internal memory including, for example, cache memory.

The system 100 described above is extensible, allowing a user with a newly defined disease-specific physiological index or novel VM to build and implement a disease-specific monitor (DSM) virtually as a software application on a web-based interface of the system 100, which also enables physiological indexes or VMs to run in real-time as data is collected and then to present results in a formatted way. The DSM capability of the system 100 allows researchers to view physiological data in new and interesting ways, for example, adding a 20-second moving average curve to a heart rate monitor or overlaying two different histograms of derived physiological measurements on to the same graph. The DSM capability enables a user to very quickly create a new monitor for a new physiological index or novel VM for predictive analytics and goal-directed therapies, enabling the rapid creation of new monitors as a grouping or reorganization of existing physiological monitors that are relevant to a specific disease;

DSMs running on the system 100 can be run in real time using existing data feeds or can be run retrospectively over archived data saved by the system 100 from the moment the patient was admitted to the unit and instrumented with monitors. In the following discussion, the term "user" refers to the developer of a DSM. In some embodiments, DSM developers may be employees or contractors of an entity providing the system 100. In other embodiments, DSM developers may include a care provider or researcher who is developing a novel VM or algorithm.

In an example usage scenario, a medical researcher discovers a new physiological relationship (e.g. an index), and wants to enable monitoring of this index in patients. The researcher's index can be computed by an algorithm whose inputs are physiological data captured by a subset of the suite of instruments in a typical clinical care setting by the system 100. The researcher has access to the system 100 through the research server 170. The researcher constructs an algorithm to compute the new index. The system 100 can access its historic archive and real time data streams for input data streams for the new index. Widgets, layout tools, and DSMs are all accessed through a web-based interface.

Figure 6:
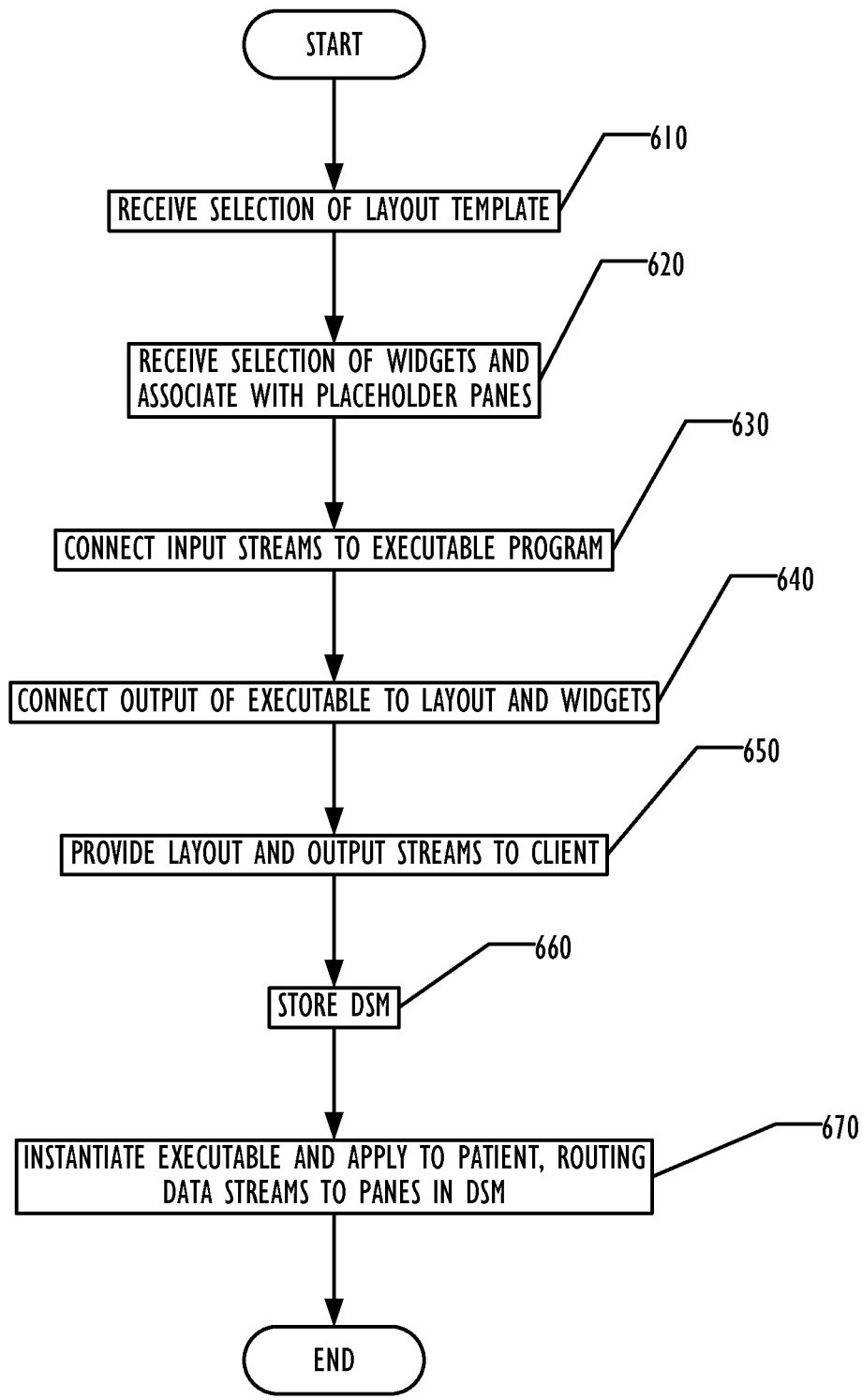
FIG. 6 is a flowchart illustrating a technique for creating a disease specific monitor according to one embodiment.

Turning to FIG. 6, a flowchart illustrates a technique for creating a DSM according to one embodiment. The system 100's DSM tool provides a set of predefined web-displayed widgets (graphs and charts) for various data types. Similarly, the DSM tool provides a set of predefined web-displayed layouts with placeholders in various points which accept instances of widgets. The DSM developer can select a specific layout template that will form the basis of the new DSM from the set of layout templates. The DSM tool receives that selection in block 610. The developer, then selects widgets and, using the DSM tool, associates placeholder panes in the display layout with instances of display widgets in block 620. The user associates the layout with the necessary widgets to an executable program which calculates the data to be fed into the system. In block 630, the DSM tool connects the desired input data streams to the executable program. In block 640 the user connects the output of the executable program to the selected display layout and widgets. In use, as indicated in block 650, the display layout and output data streams are provided to a web-based client 195 of the system 100. If the DSM is acceptable, the user can store in block 660 the information associated with the DSM, for example, the display layout, the executable program, and the I/O streams connected to the executable, giving the DSM a name. Another user, such as a clinician in a clinical trial, can now access the new DSM and associate it with a patient.

In use at block 670, the system 100 instantiates the executable commands responsible for creating the new calculated data streams and applies them to the selected patient. The system 100 then routes the new data streams from that patient to the proper panes in the new monitor on the web-enabled end-point device 195 of the user. In some embodiments, the user can customize or configure the monitor further on the client device 195.

The DSM tool allows visualization of transformed physiological and patient-related data, including both calculated data and measured data, using new types of data visualization (i.e., non-standard and novel monitor views). The DSM tool assists the user by providing modular construction of monitoring from modular reusable widgets, which allows arbitrary display or graphing of data from arbitrary data streams, and template layouts. The constructed DSMs can be either or both patient and disease specific based on the condition of the patient, as defined or determined by a care provider. Customization can be done on a per-patient basis. A doctor can prescribe a type of monitoring on a patient-by-patient basis, and the monitor data can be accessed remotely through a website interface. In one embodiment, data transformations are done on the informatics server 180, while display transformations can be done on the client 195. The modular construction of a layout allows multiple transformations to be computed in parallel for a particular patient.

Virtual monitors do not require the construction of physical devices, thus eliminating costs and unnecessary risks to the patient. Virtual monitors can be constructed in minutes whereas physical monitors may take years or decades. Thus, these techniques allow rapid DSM development, rapidly creating and implementing new DSMs as decision support tools for care providers. The DSM techniques also allow deployment and use of a DSM as a medical device, providing real-time access to these instantiated DSMs that run on the system 100 for clinical use within a critical care setting. The DSM allows coordinated patient-specific, doctor-driven risk scoring, including development and calculation of new alarms for the conditions being monitored. It provides a tool to implement one or more algorithms that have conventionally been implemented in separate and multiple special purpose devices.

Servers run the multiple applications from data routed from the system 100 to those identified applications that operate on the data. Data can be pushed back to wherever the data is needed for appropriate application processing. A collection of tools can be built for creating the indices, with the ability to send hyperlinks to allow viewing on patient data. In some embodiments, the system 100 can detect signal dropout and trigger a change in the DSM display, based on its knowledge of which signal has dropped out. Input from the clinician can be included and pushed to the patient record, using HL7, including notes, orders, etc.

These techniques have not been done previously because the data sources were historically analog devices that were not networked, making collection, analysis and use of the data difficult, even if such data was stored and available for use, which it frequently was not. Time synchronization of data drawn from various and incompatible monitors was also difficult. Bedside monitors cannot provide this functionality because they are typically analog, from various incompatible vendors, have inconsistencies in times of connection to patients and continuity of monitoring as patients are moved in the course of hospitalization, and do not cross-correlate multiple pieces of data from different, incompatible sensors. By building on top of the system 100, which allows integrating such previously non-integrated analog and serial monitors, a more flexible and powerful system can be provided in the healthcare arena.

While certain exemplary embodiments have been described in detail and shown in the accompanying drawings, it is to be understood that such embodiments are merely illustrative of and not devised without departing from the basic scope thereof, which is determined by the claims that follow.

We claim:

1. A physiological data monitoring system, comprising:
an informatics server, comprising:
one or more processors;
a memory, coupled to the one or more processors, on which instructions for creating a customized physiological monitor are stored, comprising instructions that when executed cause one or more processors to:
receive a selection of a layout template from a plurality of predefined layout templates;
receive a selection of a display widget from a plurality of predefined display widgets;
associate the selected display widget with a pane of the selected layout template;
connect a plurality of real-time physiological data streams of different types to an input of an executable program;
push an output stream of the executable program to a web browser via a websocket server;
connect the output stream of the executable program to an input of the selected display widget in the web browser; and
display the output stream of the executable program in a web-based user interface in the selected layout template by the selected display widget,
wherein the selected display widget allows display or graphing of any data stream, and
wherein the executable program calculates a new physiological index by combining a plurality of different types of physiological data using a researcher-constructed algorithm, producing a transformed data stream for displaying by the selected display widget.

2. The physiological data monitoring system of claim 1, wherein the instructions further comprise instructions that when executed cause one or more processors to:
store information associated with the selected layout, the executable program, and the input and output data streams as a physiological data monitor; and
naming the physiological data monitor.

3. The physiological data monitoring system of claim 2, wherein the instructions further comprise instructions that when executed cause one or more processors to:
provide the named physiological data monitor to a client.

4. The physiological data monitoring system of claim 3, wherein the client is a web-enabled client.

5. The physiological data monitoring system of claim 2, wherein named physiological data monitor is disease specific.

6. The physiological data monitoring system of claim 2, wherein the named physiological data monitor is patient specific.

7. The physiological data monitoring system of claim 2, wherein the instructions further comprise instructions that when executed cause one or more processors to:
receive user customization of the named physiological monitor.

8. The physiological data monitoring system of claim 1, wherein the executable program is configured to provide both calculated data and measured data output streams.

9. A non-transitory machine readable medium on which are stored instructions for creating a customized physiological monitor, comprising instructions that when executed cause one or more programmable devices to:
receive a selection of a layout template from a plurality of predefined layout templates;
receive a selection of a display widget from a plurality of predefined display widgets;
associate the selected display widget with a pane of the selected layout template;
connect a plurality of real-time physiological data streams of different types to an input of an executable program;
push an output stream of the executable program to a web browser via a websocket server;
connect the output stream of the executable program to an input of the selected display widget in the web browser; and
display the output stream of the executable program in a web-based user interface in the selected layout template by the selected display widget,
wherein the selected display widget allows display or graphing of any data stream, and
wherein the executable program calculates a new physiological index by combining a plurality of different types of physiological data using a researcher-constructed algorithm, producing a transformed data stream for displaying by the selected display widget.

10. The machine readable medium of claim 9, wherein the instructions further comprise instructions that when executed cause one or more processors to
store information associated with the selected layout, the executable program, and the input and output data streams as a physiological data monitor; and
name the physiological data monitor.

11. The machine readable medium of claim 10, wherein the instructions further comprise instructions that when executed cause one or more processors to:
provide the named physiological data monitor to a client.

12. The machine readable medium of claim 11, wherein the client is a web-enabled client.

13. The machine readable medium of claim 10, wherein the named physiological data monitor is disease specific.

14. The machine readable medium of claim 10, wherein the named physiological data monitor is patient specific.

15. The machine readable medium of claim 10, wherein the instructions further comprise instructions that when executed cause one or more processors to:
receive user customization of the named physiological monitor.

16. The machine readable medium of claim 9, wherein the executable program is configured to provide both calculated data and measured data output streams.

17. A method of designing customized physiological monitors, comprising:
selecting a layout template from a plurality of predefined layout templates;
selecting a display widget from a plurality of predefined display widgets;
associating the selected display widget with a pane of the selected layout template;
connecting a plurality of real-time physiological data stream as an input data stream of an executable program;
pushing an output stream of the executable program to a web browser via a websocket server;
connecting the output data stream of the executable program to an input of the selected display widget in the web browser; and
displaying the output stream of the executable program in a web-based user interface in the selected layout template by the selected display widget,
wherein the selected display widget allows display or graphing of any data stream, and
wherein the executable program calculates a new physiological index by combining a plurality of different types of physiological data using a researcher-constructed algorithm, producing a transformed data stream for displaying by the selected display widget.

18. The method of claim 17, further comprising:
storing information associated with the selected layout template, the selected display widget, the association of the display widget with the pane of the selected layout template, the executable program, and the connected input and output data streams as a physiological data monitor; and
naming the stored physiological data monitor.

19. The method of claim 18, further comprising:
providing the named physiological data monitor to a web-enabled client; and
associating the named physiological data monitor with a patient.

20. The method of claim 18, wherein the stored physiological data monitor is disease specific.

21. The physiological data monitoring system of claim 1, wherein the instructions further comprise instructions that when executed cause the one or more processors of the informatics server to:
connect an historical physiological data stream to another input of the executable program.

22. The machine readable medium of claim 9, wherein the instructions further comprise instructions that when executed cause the one or more processors to:
connect an historical physiological data stream to another input of the executable program.

23. The method of claim 17, further comprising:
connecting an historical physiological data stream to another input of the executable program.

* * * * *